United States Patent [19]

Fujino et al.

[11] 3,972,859
[45] Aug. 3, 1976

[54] NOVEL DECAPEPTIDE AMIDE ANALOGS OF LEUTEINIZING HORMONE-RELEASING HORMONE

[75] Inventors: Masahiko Fujino, Takarazuka; Susumu Shinagawa, Osaka; Tsunehiko Fukuda, Suita, all of Japan

[73] Assignee: Takeda Chemical Industries, Ltd., Osaka, Japan

[22] Filed: Mar. 4, 1975

[21] Appl. No.: 555,126

[30] Foreign Application Priority Data
Mar. 8, 1974    Japan.............................. 49-27442

[52] U.S. Cl. ...................... 260/112.5 LH; 424/177
[51] Int. Cl.² ................. C07C 103/52; A61K 37/00
[58] Field of Search............................ 260/112.5 LH

[56] References Cited
UNITED STATES PATENTS

| | | | |
|---|---|---|---|
| 3,835,108 | 9/1974 | Immer et al. | 260/112.5 LH |
| 3,896,104 | 7/1975 | McKinley et al. | 260/112.5 LH |

Primary Examiner—Lewis Gotts
Assistant Examiner—Reginald J. Suyat
Attorney, Agent, or Firm—Wenderoth, Lind & Ponack

[57] ABSTRACT

The novel decapeptide amide derivatives of the formula (Pyr)Glu-His-Trp-Ser-$R_1$-$R_2$-$R_3$-Arg-Pro-Gly-$NH_2$ 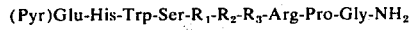

wherein $R_1$ is Tyr or Phe; $R_2$ is D-Nle, D-Nva, D-Abu, D-Phe, D-Ser, D-Thr or D-Met and $R_3$ is Leu, Ile or Nle have a strong ovulation inducing activity.

14 Claims, No Drawings

NOVEL DECAPEPTIDE AMIDE ANALOGS OF LEUTEINIZING HORMONE-RELEASING HORMONE

DECAPEPTIDE AMIDES

The present invention relates to novel decapeptide amide derivatives having strong ovulation inducing activity, which are represented by the formula:

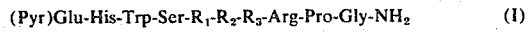

(Pyr)Glu-His-Trp-Ser-R$_1$-R$_2$-R$_3$-Arg-Pro-Gly-NH$_2$     (I)

wherein R$_1$ is Tyr or Phe; R$_2$ is D-Nle, D-Nva, D-Abu, D-Phe, D-Ser, D-Thr or D-Met and R$_3$ is Leu, Ile or Nle.

The present invention relates also to a method for producing the decapeptide amide derivatives (I).

In the present specification and the claims, amino acids and peptides and their activated carboxyl or protective groups are designated by abbreviations which are in common usage in the particular field of art or which have been approved by Committee on Biochemical Nomenclature of IUPAC-IUB. Amino acid is in the L-configuration unless otherwise designated.

The following abbreviations are used, for instance.
Abu: α-Aminobutyric acid
Arg: Arginine
BOC: t-Butoxycarbonyl
Bzl: Benzyl
DCC: N,N'-Dicyclohexylcarbodiimide
Gly: Glycine
His: Histidine
HONB: N-Hydroxy-5-norbornene-2,3-dicarboximide
Ile: Isoleucine
Leu: Leucine
Nle: Norleucine
Nva: Norvaline
Met: Methionine
OMe: Methyl ester
OBzl: Benzyl ester
ONB: N-Hydroxy-5-norbornene-2,3-dicarboximide ester
OSu: N-Hydroxysuccinimide ester
Phe: Phenylalanine
Pro: Proline
(Pyr)Glu: Pyroglutamic acid
Ser: Serine
Thr: Threonine
Tos: Tosyl
Trp: Tryptophan
Tyr: Tyrosine It was known for many years that the hypothalamus contains factors which, at a higher level, control the secretion of tropic hormones from the pituitary. Subsequent to the isolation of a thyrotropin-releasing hormone (TRH), luteinizing hormone releasing hormone (LH-RH) has been extracted in pure form from pigs and sheep and shown to be a decapeptide of the structure: (Pyr)Glu-His-Trp-Ser-Tyr-Gly-Leu-Arg-Pro-Gly-NH$_2$. [A. V. Schally et al., Biochem. Biophys. Res. Commun., 43, 1334(1971): R. Guillemin et al., Proc. Nat. Acad. Sci., U.S.A., 69, 278(1972)]. This finding has been followed by the synthesis of a number of similar peptides and biological tests have also been performed on these analogous peptides. However, even a minor modification in the above amino acid composition diminishes seriously the physiological activity of the peptide and the above chemical structure has been considered to be essential to the genesis of maximal physiological activity. [A. V. Schally et al., Biochem. Biophys. Res. Commun., 4, 366 (1972)].

Recently Monahan et al published in "Biochemistry", vol. 12, No. 23, pages 4616–4620(1973) that among the LH-RH analogs such as [Ala$^6$]LH-RH, [D-Ala$^6$]LH-RH, [Val$^6$]LH-RH, [D-Val$^6$]LG-RH, [Pro$^6$]LH-RH and [D-Pro$^6$]LH-RH which were synthesized by them, the [D-Ala$^6$]LH-RH exhibited the strongest activity to be 350–450 % of the potency of the parent LH-RH. The literature teaches further that LH-RH analogs having at the 6-position D-amino acid with larger bulk of side chains than D-Ala are less potent than the parent hormone. In spite of the state of the art mentioned above, the present inventors synthesized the polypeptides (I) having at the 6-position D-amino acid with larger bulk of side chains than D-Ala and tested for their LH-RH activity and found unexpectedly that the present polypeptides (I) are at least 1,000 % more potent than parent LH-RH. The present invention is the culmination of those unexpected findings.

Therefore, it is the main object of the present invention to provide novel decapeptide amide derivatives (I) which have strong ovulation inducing activity.

Another object of the present invention is to provide a method for the production of the decapeptide amide derivatives (I).

Further objects of the present invention will be made clear in accordance with the description mentioned hereinafter in this specification.

The decapeptide amide derivative (I) is produced by a method characterized by that a reagent (A) — L-Pyroglutamic acid or a peptide fragment which has an L-pyroglutamic acid unit (i.e. (Pyr)Glu-) at its N-terminal end and at the same time which, from thereon, comprises the above amino acid sequence — is condensed with a reagent (B) — an amine component which corresponds to the balance of the decapeptide amide derivative (I) — the two reagents (A) and (B) being optionally protected by a protecting group or groups, and then the protecting group or groups if any are removed.

Thus, the reagent (A) is L-pyroglutamic acid or a peptide fragment which has an L-pyroglutamic acid unit at its N-terminal end and at the same time which from thereon comprises amino acid sequence of formula (I), and the reagent (B) to be condensed with the reagent (A) is an amine component which corresponds to the balance of the decapeptide amide derivative (I), the reagents (A) and (B) being optionally protected.

Basic combinations of the reagent (A) and the reagent (B) are exemplified in the following Table 1.

Table 1

| Combination | Reagent (A) | (B) |
|---|---|---|
| 1 | (Pyr)Glu-OH | H-His-Trp-Ser-R$_1$-R$_2$-R$_3$-Arg-Pro-Gly-NH$_2$ |
| 2 | (Pyr)Glu-His-OH | H-Trp-Ser-R$_1$-R$_2$-R$_3$-Arg-Pro-Gly-NH$_2$ |
| 3 | (Pyr)Glu-His-Trp-OH | H-Ser-R$_1$-R$_2$-R$_3$-Arg-Pro-Gly-NH$_2$ |
| 4 | (Pyr)Glu-His-Trp-Ser-OH | H-R$_1$-R$_2$-R$_3$-Arg-Pro-Gly-NH$_2$ |
| 5 | (Pyr)Glu-His-Trp-Ser-R$_1$-OH | H-R$_2$-R$_3$-Arg-Pro-Gly-NH$_2$ |
| 6 | (Pyr)Glu-His-Trp-Ser-R$_1$-R$_2$-OH | H-R$_3$-Arg-Pro-Gly-NH$_2$ |

Table 1-continued

| Combination | Reagent (A) | (B) |
|---|---|---|
| 7 | (Pyr)Glu-His-Trp-Ser-$R_1$-$R_2$-$R_3$-OH | H-Arg-Pro-Gly-$NH_2$ |
| 8 | (Pyr)Glu-His-Trp-Ser-$R_1$-$R_2$-$R_3$-Arg-OH | H-Pro-Gly-$NH_2$ |
| 9 | (Pyr)Glu-His-Trp-Ser-$R_1$-$R_2$-$R_3$-Arg-Pro-OH | H-Gly-$NH_2$ |
| 10 | (Pyr)Glu-His-Trp-Ser-$R_1$-$R_2$-$R_3$-Arg-Pro-Gly-OH | $NH_3$ |

It has also been known that a protected L-glutamyl group shown by the general formula (II):

$$R_4CO-CH_2CH_2CH(NH_2)CO- \quad (II)$$

[wherein $R_4$ is an alkoxy group (e.g. methoxy, ethoxy, n-propoxy, i-propoxy, n-butoxy, etc.), an aralkyloxy group (e.q. benzyloxy, etc.) or amino] is easily converted to the L-pyroglutamyl group itself:

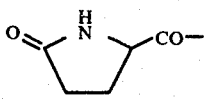

by the contact with a base (e.g. ammonia, etc.) or an acid (e.g. acetic acid etc.) and that the group (II) is equivalent to L-pyroglutamyl group itself in this respect. In the method of the present invention, it is to be construed that the L-pyroglutamyl (i.e. (Pyr)Glu-) of the reagent (A) includes not only the L-pyroglutamyl group itself but also the protected L-glutamyl group of the formula (II). In case when (Pyr)Glu- of the reagent (A) represents the group (II), the group (II) is easily converted to L-pyroglutamyl group itself in accordance with per se known means.

The condensation reaction according to this invention can be carried out by condensing means known for the formation of peptide linkages. Among such means of condensation are DCC/HONB process [Belgian Pat. No. 796,399], the azide process, chloride process, acid anhydride process, mixed acid anhydride process, DCC process, active ester process, Woodward reagent K process, carbodiimidazole process, oxidation-reduction process and others [The Peptides, Vol.1(1966), Schröder and Lubke, Academic Press, New York, U.S.A.].

Prior to the condensation reaction, one may protect the carboxyl and amino groups which should not be involved in the contemplated reaction or activate the carboxyl or/and amino groups which will take part in the reaction, by means which are known per se. The carboxyl groups in the starting material may be protected in the form of metal salts (e.g. sodium and potassium salts) or esters (e.g. methyl, ethyl, benzyl, p-nitrobenzyl, t-butyl or t-amyl esters).

Protective groups for amino groups in the starting materials may be any of conventional protecting groups of amino groups in peptide synthesis, e.g. benzyloxycarbonyl, t-butoxycarbonyl, isobornyloxycarbonyl, etc. The imino group of histidine may be protected with any of conventional protecting group such as benzyl, tosyl, 2,4-dinitrophenol, t-butoxycarbonyl or carbobenzoxy. The hydroxyl group of serine may be protected with a conventional protective group such as benzyl, t-butyl and other ether-forming groups. The hydroxyl group of tyrosine may be protected with benzyl, t-butyl and other ether-forming groups; the guanidino group of arginine may be protected with such groups as nitro, tosyl, carbobenzoxy, isobornyloxycarbonyl or adamantyloxycarbonyl. As examples of activated carboxyl groups in starting materials, there may be mentioned the corresponding acid anhydride, azide, active esters [esters with alcohols (e.g. pentachlorophenol, 2,4,5-trichlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide or N-hydroxybenztriazole)], etc. The activated amino groups in starting materials may for example be the corresponding phosphoric acid amide.

The following table shows some exemplary combinations of such forms of carboxyl and amino groups in materials (A) and (B).

Table 2

| Exemplary combinations | Starting Material (A) | | (B) | |
|---|---|---|---|---|
| | COOH | $NH_2$ | COOH | $NH_2$ |
| 1* | Free | Protected | Protected | Free |
| 2 | Activated | Protected | Free | Free |
| 3 | Free | Protected | Protected | Activated |

(Note) In the case designated by an asterisk*, a dehydrating agent (e.g. a carbodiimide reagent such as dicyclohexyl-carbodiimide) is preferably present in the reaction system. A mode of practice of this invention may be written as follows.

(Pyr)Glu-His-Trp + Ser-$R_1$-Protective group
↓ Condensation (e.g. DCC/HONB)
(Pyr)Glu-His-Trp-Ser-$R_1$-Protective group
↓ Removal of a protective group (e.g. catalytic reduction with Pd catalyst)
(Pyr)Glu-His-Trp-Ser-$R_1$ $$\underset{|}{NO_2}$$
Z-$R_2$-$R_3$-Arg-Pro-Gly-$NH_2$
↓ Removal of a protective group (e.g. in the presence of HBr)
$$\underset{|}{NO_2}$$
$R_2$-$R_3$-Arg-Pro-Gly-$NH_2$

Table 2-continued

| Exemplary combinations | Starting Material | | | |
|---|---|---|---|---|
| | (A) | | (B) | |
| | COOH | NH₂ | COOH | NH₂ |

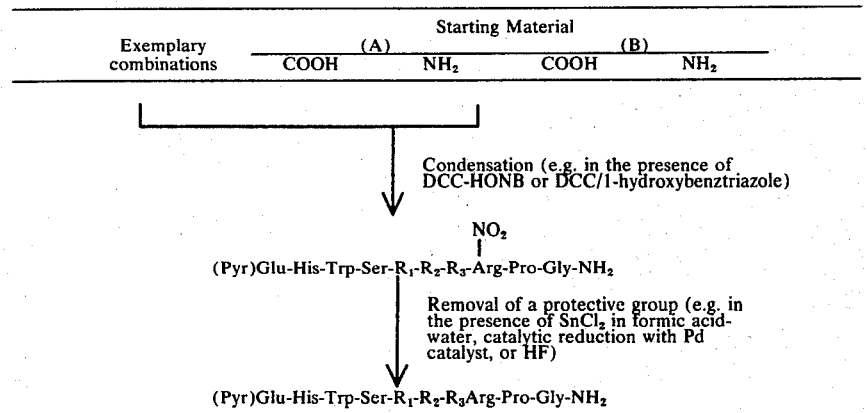

This reaction may be conducted in the presence of a solvent. The solvent can be selected from those known to be useful for peptide condensation reactions. Thus, anhydrous or aqueous dimethylformamide, dimethylsulfoxide, pyridine, chloroform, dioxane, dichloromethane, tetrahydrofuran and suitable mixtures of such solvents may be mentioned by way of example.

The reaction temperature is selected from within the range known to be emloyable for reactions leading to the formation of peptide bonds, i.e. normally within the range of about $-20°C$ to about $30°C$. Further, the precursor materials (protected peptides) of the contemplated compounds according to this invention may also be easily prepared by solid-phase synthetic processes.

After the contemplated condensation reaction has been completed, if the product carries protective groups, they can be removed by routine procedures. Among such routine procedures are catalytic reduction in the presence of a catalyst such as palladium black, palladium-on-carbon, platinum or the like, solvolysis by means of hydrogen fluoride, trifluoroacetic acid or the like, and reduction with metallic sodium in liquid ammonia.

The peptide (I) thus produced can be recovered from the reaction product mixture by procedures known for the recovery of peptides, e.g. by extraction, distribution, column chromatography, etc.

The present reaction may be carried out by per se conventional solid phase method.

The peptide (I) may also be recovered in the form of a salt or metal complex compound.

As acids which are able to form salts with peptide (I), there may be mentioned inorganic acids such as hydrochloric acid, hydrobromic acid, perchloric acid, nitric acid, thiocyanic acid, sulfuric acid, phosphoric acid, etc. and organic acids such as formic acid, acetic acid, propionic acid, glycolic acid, lactic acid, pyruvic acid, oxalic acid, malonic acid, succinic acid, maleic acid, fumaric acid, anthranylic acid, cinnamic acid, naphthalenesulfonic acid or sulfanylic acid, for instance.

The metals which are able to form metal complex compounds with peptide (I) include, among others, zinc, nickel, cobalt, copper and iron. Such a metal complex compound can be produced by conventional procedures, for example, by reacting peptide (I) with the hydroxide or oxide of a metal of the above-mentioned variety at pH about 6 to 8.

The polypeptides (I) according to this invention have the LH-RH (luteinizing hormone releasing hormone) activity and, accordingly, are able to promote the secretion of LH (luteinizing hormone) and FSH (follicle stimulating hormone). Therefore, polypeptides (I) are of use as drugs for promoting ovulations in women and other animals (e.g. rats, ewes, pigs, cows, mares, quails or hens). The peptides can also be used for other pharmaceutical purposes for which conventional LH-RH, LH and FSH preparations have been employed.

Since the LH-RH activity of polypeptides (I) is about 10 to 25 times that of known naturally-occurring LH-RH, their dosage may be determined for each application on the basis of the above multiple whilst other factors (e.g. the subject of administration or the kind of disease) are also taken into consideration. For example, a suitable dosage may be selected from within the range of about 5 ng. (nano grams) to 10 $\mu$g. daily per kilogram of body weight.

Polypeptides (I) are primarily administered nonorally (e.g. by injection or by the rectal or vaginal route), although they are orally administered in certain instances.

The dosage forms employable include, for example, injections, suppositories, pessaries and powders. The injections can be prepared by dissolving about 10$\gamma$ to 500$\gamma$ of a polypeptide (I) in 1 m. of physiological saline. Polypeptides (I) can be also made into lyophilized ampoule products with mannitol added as an excipient so that one may administer them as injections for extemporaneous use.

The starting material peptides employable in the method of this invention can be prepared either by known processes for peptide synthesis or by utilizing such procecces as found necessary.

For further illustration of the invention, examples are given as follows:

In the examples, the following abbreviations mean Rf value of a thin layer chromatography on silica gel with the following solvent system:

$Rf^1$: chloroform - methanol - acetic acid, 9:1:0.5
$Rf^2$: ethyl acetate - pyridine - acetic acid - water, 30:10:3:5
$Rf^3$: n-butanol - ethyl acetate - acetic acid - water, 1:1:1:1

EXAMPLE 1

Production of
(Pyr)Glu-His-Trp-Ser-Phe-(D)-Nva-Leu-Arg-Pro-Gly-NH₂ a. Preparation of Z-(D)-Nva-Leu-Arg(NO₂)-Pro-Gly-NH₂

To a solution of Z-(D)-Nva-OH(380 mg), H-Leu-Arg(NO₂)-Pro-Gly-NH₂ (690 mg.) and HONB (300 mg.) in 5 ml. of dimethylformamide is added 340 mg. of DCC at 0°C with stirring. The mixture is stirred for 2 hours at 0°C and for additional 10 hours at room temperature. The reaction mixture is filtered to remove the formed dicyclohexyl-urea, and the filtrate is evaporated to dryness. The resulting residue is dissolved in 100 ml. of chloroform and the solution is washed with 4 % aqueous sodium bicarbonate solution and water. The washed solution is dried over anhydrous magnesium sulfate and evaporated to dryness. The residue is then triturated with a mixture of ethylacetate (25 ml.) and ether (25 ml.) to give a white powder, which is collected by filtration and reprecipitated from ethanol-ether: yield, 1.12 g., $[\alpha]_D^{23}$—50.5°(c=1.1 in Methanol), $Rf^1$=0.32.

Analysis for $C_{32}H_{52}O_9N_{10}$. calcd: C, 53.32; H, 7.27; N, 19.43. Found: C, 53.49; H, 7.56; N, 19.19.

b. Preparation of (Pyr)Glu-His-Trp-Ser-Phe-(D)-Nva-Leu-Arg-Pro-Gly-NH₂

Z-(D)-Nva-Leu-Arg(NO₂)-Pro-Gly-NH₂ (1.0 g.) is dissolved in 10 ml. of 25 % of hydrogenbromide in acetic acid, and the solution is stirred for 50 minutes. The reaction mixture is diluted with 200 ml. of dry ether to give a precipitate, which is collected by filtration and washed well with dry ether. The collected powder is dried over sodium hydroxide under reduced pressure. This powder is dissolved in 10 ml. of dimethylformamide together with (Pyr)Glu-His-Trp-Ser-Phe-OH(1.0 g.) and HONB (440 mg.). The solution is cooled to 0°C and to this is added DCC (400 mg.) with stirring. The mixture is stirred for 6 hours at 0°C and for additional 16 hours at room temperature. The reaction mixture is filtered to remove the formed dicyclohexyl-urea, and the filtrate is triturated with addition of 100 ml. of ether to give a precipitate, which is collected by filtration. The collected precipitate is dissolved in 10 % aqueous ethanol and the solution is applied on a column of polystyrene resin [Amberlite XAD-2(150–250 mesh, 3.5 × 25 cm), Rohm & Haas Co. Ltd. U.S.A.,] and the column is eluated by a gradient elution method with 10 % aqueous ethanol and 100 % ethanol (500:550 ml.). The principal fraction (380–520 ml.) is collected and evaporated to dryness. The residue is dissolved in 5 ml. of hot methanol and reprecipitated by addition of ethylacetate to give the protected decapeptide amide. 1.41 g., $[\alpha]_D^{24}$—35.4° (c=0.12, in methanol), $Rf^2$=0.20, $Rf^3$=0.56.

The protected decapeptide amide (500 mg.) is dissolved in 5 ml. of anhydrous hydrogen fluoride together with 0.5 ml. of anisole at −70°C. After being stirred for 30 minutes at −5°C, hydrogen fluoride is removed by evaporation. The resulting residue is dissolved in 20 ml. of water, and the solution is extracted twice with 10 ml. of ethyl acetate. The aqueous layer is applied on a column of carboxymethylcellulose (2 × 33 cm) and the column is eluated by a gradient elution method using an ammonium acetate buffer as eluate [0.005M, pH 6.8(500 ml.) - 0.2M, pH 6.8(500 ml.)]. The principal fraction (420 ml. - 680 ml.) is collected and lyophilized to give a white powder. yield 380 mg., $[\alpha]_D^{22}$—32.4°(c=0.52, in 5 % acetic acid), $Rf^2$=0.05, $Rf^3$=0.68.

Amino acid analysis: His 1.01; Arg 0.98; Trp 0.87; Ser 0.94; Glu 1.00; Pro 1.02; Gly 1.00; Nva 1.01; Leu 1.00; Phe 0.97 (peptide content, 84 %).

EXAMPLE 2

Production of (Pyr)Glu-His-Trp-Ser-Tyr-(D)-Nle-Leu-Arg-Pro-Gly-NH₂ by solid-phase procedure a. Preparation of BOC-Gly-resin In 60 ml. of chloroform-ethanol (2:1) is placed 10 g. of chloromethyl-resin (Cl content 2.0 m mol/g.), followed by the addition of 10.5 g. of BOC-Gly and 8.4 ml. of triethylamine. The mixture is stirred at room temperature for 1.5 hours and, then, heated for 24 hours. The resin is recovered by filtration and washed well with dimethylformamide and further with ethanol, water, ethanol and ether in the order mentioned and dried. Yield 17.55 g. Amino acid analysis shows that this resin contains 0.88 millimols/gram of BOC-Gly.

b. Preparation of (Pyr)Glu-His(Tos)-Trp-Ser(Bzl)-Tyr-(Bzl)-D-Nle-Leu-Arg(Tos)-Pro-Gly-resin The reaction tank of an automatic peptide synthesizer (Model: APS-800 of Simadzu Seisakusho K.K., Japan) is charged with 2.177 g. of BOC-Gly-resin which is obtained in the above a) and caused to swell with dichloromethane for 12 hours. Then, the following amino acids are fed on the cycle given below.

BOC-Pro, BOC-Arg(Tos), BOC-Leu, BOC-D-Nle, BOC-Tyr(Bzl), BOC-Ser(Bzl), BOC-Trp, BOC-His(-Tos), (Pyr)Glu.

Dichloromethane (3 minutes × 3) → 50 % trifluoroacetic acid/dichloromethane (10 min. and 30 min.) → dichloromethane (3 min. × 3) → ethanol (3 min. × 3) → dichloromethane (3 min. × 3) → 10 % triethylamine/chloroform(10 min.) → chloroform (3 min. × 3) → dichloromethane (3 min. × 2) → BOC-amino acid-anhydride (synthesized from BOC-amino acid and DCC by routine procedure) (30 min. and 60 min.) → acetylation (with acetic anhydride in dichloromethane and triethylamine) (1 hour) → dichloromethane (3 min. × 3) [only (Pyr)Glu is directly condensed with DCC in dimethylformamide].

Finally, the resin is washed with ethanol, chloroform and dimethylformamide. Then, it is washed with ether and dried. Yield 6.20 g.

c. Preparation of (Pyr)Glu-His-(Tos)-Trp-Ser(Bzl)-Tyr(Bzl)-D-Leu-Leu-Arg(Tos)-Pro-Gly-NH₂

In 50 ml. of ammonia-saturated methanol is suspended 2.622 g. of the resin prepared in b) and the suspension is sitrred at room temperature for 70 hours.

The resin is recovered by filtration and washed with dimethylformamide. The filtrate and washings are pooled, concentrated to dryness under reduced pressure and treated with ether. The procedure gives 1.187 g. of crude powder.

A 588 mg. portion of this product is purified on a dry column of 50 g. of silica gel using as a developer a solvent mixture of methanol and chloroform, whereupon 186 mg. of contemplated product is obtained.

d. Preparation of (Pyr)Glu-His-Trp-Ser-Tyr-D-Leu-Leu-Arg-Pro-Gly-NH₂

In the presence of 0.2 ml. of anisole and 0.2 ml. of mercaptoethanol, 173.3 mg. of the protected peptide obtained in c) is dissolved in 5 ml. of dry hydrogen fluoride and the solution is stirred at 0°C for 1 hour. It is then concentrated to dryness under reduced pressure and the concentrate is dissolved in 20 ml. of water. The insolubles are filtered off and the filtrate is run down a column (1.5 cm dia. × 20 cm) of strongly basic anion exchange resin (Amberlite IRA-410 acetate-form, Rohm & Haas Co.Ltd.U.S.A.) Then, the effluent is purified by means of carboxyl-methylcellulose (1.5 × 22 cm; the gradient elution method using 0.005 M to 0.2 M ammonium acetate of pH 6.8) and polystyrene resin (Amberlite XAD-2, Rohm & Haas Co.Ltd.U.S.A.) (1.5 × 7.5 cm; the gradient elution method using 5 % to 70 % aqueous ethanol). The eluate is further subjected to gelfiltration chromatography on Sephadex LH-20 (Pharmacia Fine Chemicals, Sweden) (0.9 × 53.5 cm; 0.1 N acetic acid). The procedure gives 39 mg. of contemplated compound. $[\alpha]_D^{24}$ −40.5°(c=0.5 in 5 % aqueous acetic acid)

Amino acid analysis (acid hydrolysis in the presence of thioglycolic acid): Glu 0.97; His 0.97; Trp 0.94; Ser 0.88; Tyr 1.0; Leu 1.00; Nle 1.06; Arg. 1.03; Pro 1.00; Gly 1.03 (87 % recovery)

EXAMPLES 3–13

When similar procedures to those in Example 2 are followed except for employing starting materials listed in the following table in place of those in Example 2, the decapeptide amides (I) are produced as listed in the table.

Table

| Example | Decapeptide amide (I) R₁ | R₂ | R₃ | $[\alpha]_D^{24}$ (c=0.5 in 5% aqueous acetic acid) | Amino acid analysis | Starting materials employed in place of Example 2 BOC-Tyr-(Bzl) | BOC-D-Nle | BOC-Leu |
|---|---|---|---|---|---|---|---|---|
| 3 | Tyr | D-Ser | Leu | −44.8° | His 1.02; Arg 1.01; Trp 0.97; Ser 1.91; Glu 1.00; Pro 1.01; Gly 1.03; Leu 0.97; Tyr 0.96 | BOC-Tyr(Bzl) | BOC-D-Ser (Bzl) | BOC-Leu |
| 4 | Tyr | D-Abu | Leu | −43.2° | His 0.96; Arg 1.00; Trp 0.89; Ser 0.92; Glu 1.00; Pro 1.00; Gly 0.99; Abu 0.97; Leu 1.00; Tyr 0.98 | BOC-Tyr(Bzl) | BOC-D-Abu | BOC-Leu |
| 5 | Tyr | D-Nva | Leu | −38.9° | His 1.00; Arg 0.99; Trp 0.92; Ser 0.91; Glu 1.00; Pro 1.00; Gly 1.01; Nva 0.97; Leu 0.98; Tyr 0.98 | BOC-Tyr(Bzl) | BOC-D-Nva | BOC-Leu |
| 6 | Tyr | D-Thr | Leu | −37.5° | His 1.01; Arg 0.98; Trp 0.95; Thr 1.00; Ser 0.92; Glu 1.00; Pro 1.00; Gly 0.99; Leu 1.00; Tyr 0.98 | BOC-Tyr(Bzl) | BOC-D-Thr | BOC-Leu |
| 7 | Tyr | D-Phe | Leu | −52.4° | His 1.00; Arg 0.99; Trp 0.87; Ser 0.89; Glu 1.00; Pro 0.99; Gly 1.01; Leu 0.98; Phe 1.00; Tyr 0.96 | BOC-Tyr(Bzl) | BOC-D-Phe | BOC-Leu |
| 8 | Tyr | D-Met | Leu | −42.0° | His 0.98; Arg 1.00; Trp 0.89; Ser 0.92; Glu 0.99; Pro 0.98 Gly 1.00; Met 0.79; Leu 1.00; Tyr 1.00 | BOC-Tyr(Bzl) | BOC-D-Met | BOC-Leu |
| 9 | Phe | D-Phe | Leu | −69.5° | His 1.00; Arg 0.98; Trp 0.87; Ser 0.98; Glu 1.01; Pro 0.98; Gly 1.00; Leu 1.00; Phe 1.98 | BOC-Phe | BOC-D-Phe | BOC-Leu |
| 10 | Tyr | D-Abu | Ile | −38.5° | His 1.00; Arg 1.00; Trp 0.92; Ser 0.88; Glu 1.03; Pro 1.00; Gly 1.00; Abu 0.96; Ile 0.98; Tyr 0.98 | BOC-Tyr(Bzl) | BOC-D-Abu | BOC-Ile |
| 11 | Phe | D-Ser | Nle | −32.5° | His 0.96; Arg 0.94; Trp 0.87; Ser 1.87; Glu 1.00; Pro 0.99; Gly 1.00; Nle 0.96; Phe 1.02 | BOC-Phe | BOC-D-Ser (Bzl) | BOC-Nle |
| 12 | Phe | D-Nle | Nle | −35.1° | His 1.00; Arg 1.01; Trp 0.81; Ser 0.89; Glu 1.02; Pro 1.00; Gly 1.00; Nle 2.03; Phe 0.97 | BOC-Phe | BOC-D-Nle | BOC-Nle |
| 13 | Phe | D-Nva | Ile | −35.5° | His 0.96; Arg 1.00 Trp 0.86; Ser 0.89; Glu 1.00; Pro 1.00; Gly 0.98; Nva 0.90; Ile 0.92; Phe 0.99 | BOC-Phe | BOC-D-Nva | BOC-Ile |

What is claimed is:

1. A compound of the formula

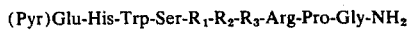

(Pyr)Glu-His-Trp-Ser-R₁-R₂-R₃-Arg-Pro-Gly-NH₂ wherein $R_1$ is Tyr or Phe; $R_2$ is D-Nle, D-Nva, D-Abu, D-Phe, D-Ser, D-Thr or D-Met and $R_3$ is Leu, Ile or Nle.

2. The compound as claimed in claim 1, wherein $R_1$ is Tyr, $R_2$ is D-Nle and $R_3$ is Leu.

3. The compound as claimed in claim 1, wherein $R_1$ is Tyr, $R_2$ is D-Ser and $R_3$ is Leu.

4. The compound as claimed in claim 1, wherein $R_1$ is Tyr, $R_2$ is D-Abu and $R_3$ is Leu.

5. The compound as claimed in claim 1, wherein $R_1$ is Tyr, $R_2$ is D-Nva and $R_3$ is Leu.

6. The compound as claimed in claim 1, wherein $R_1$ is Tyr, $R_2$ is D-Thr and $R_3$ is Leu.

7. The compound as claimed in claim 1, wherein $R_1$ is Tyr, $R_2$ is D-Phe and $R_3$ is Leu.

8. The compound as claimed in claim 1, wherein $R_1$ is Tyr, $R_2$ is D-Met and $R_3$ is Leu.

9. The compound as claimed in claim 1, wherein $R_1$ is Phe, $R_2$ is D-Phe and $R_3$ is Leu.

10. The compound as claimed in claim 1, wherein $R_1$ is Tyr, $R_2$ is D-Abu and $R_3$ is Ile.

11. The compound as claimed in claim 1, wherein $R_1$ is Phe, $R_2$ is D-Ser, $R_3$ is Nle.

12. The compound as claimed in claim 1, wherein $R_1$ is Phe, $R_2$ is D-Nle, $R_3$ is Nle.

13. The compound as claimed in claim 1, wherein $R_1$ is Phe, $R_2$ is D-Nva, $R_3$ is Ile.

14. The compound as claimed in claim 1, wherein $R_1$ is Phe, $R_2$ is D-Nva, $R_3$ is Leu.

* * * * *